US008353861B2

(12) United States Patent
Tobinaga et al.

(10) Patent No.: US 8,353,861 B2
(45) Date of Patent: Jan. 15, 2013

(54) APPLICATOR FOR APPLYING FUNCTIONAL SUBSTANCES INTO HUMAN SKIN (75) Inventors: Yoshikazu Tobinaga, Shiga (JP); Susumu Sugiyama, Aichi (JP)

(73) Assignees: TEXMAC, Inc., Charlotte, NC (US); Nano Device and System Research Inc., Kyoto (JP)

( * ) Notice: Subject to any disclaimer, the term of this patent is extended or adjusted under 35 U.S.C. 154(b) by 2434 days.

(21) Appl. No.: 10/666,581

(22) Filed: Sep. 18, 2003

(65) Prior Publication Data
US 2005/0065463 A1    Mar. 24, 2005

(51) Int. Cl.
*A61M 37/00*    (2006.01)
(52) U.S. Cl. ......................................................... 604/46
(58) Field of Classification Search .................... 604/21, 604/191, 47, 46, 272, 27, 290; 600/345
See application file for complete search history.

(56) References Cited

U.S. PATENT DOCUMENTS

| 4,206,757 | A | 6/1980 | Grandadam et al. .......... 128/260 |
| 4,837,049 | A | 6/1989 | Byers et al. ...................... 427/96 |
| 4,923,421 | A | 5/1990 | Brodie et al. ...................... 445/24 |
| 5,364,374 | A | 11/1994 | Morrison et al. ............. 604/272 |
| 5,457,041 | A | 10/1995 | Ginaven et al. ............ 435/172.1 |
| 5,591,139 | A | 1/1997 | Lin et al. ........................ 604/264 |
| 5,605,694 | A | 2/1997 | Nadaud et al. ................ 424/401 |
| 5,697,901 | A | 12/1997 | Eriksson .......................... 604/46 |
| 6,124,274 | A | 9/2000 | Schehlmann et al. .......... 514/99 |
| 6,207,400 | B1 | 3/2001 | Kwon ............................... 435/14 |
| 6,219,574 | B1 | 4/2001 | Cormier et al. .................. 604/20 |
| 6,230,051 | B1 | 5/2001 | Cormier et al. .................. 604/20 |
| 6,290,991 | B1 | 9/2001 | Roser et al. |
| 6,322,808 | B1 | 11/2001 | Trautman et al. ............. 424/448 |
| 6,334,856 | B1 | 1/2002 | Allen et al. |
| 6,503,231 | B1 | 1/2003 | Prausnitz et al. |
| 6,565,532 | B1 | 5/2003 | Yuzhakov et al. |
| 6,611,707 | B1 | 8/2003 | Prausnitz et al. |
| 6,623,457 | B1 | 9/2003 | Rosenberg |
| 6,821,281 | B2 * | 11/2004 | Sherman et al. .............. 606/131 |
| 2002/0082543 | A1 * | 6/2002 | Park et al. ........................ 604/21 |

(Continued)

FOREIGN PATENT DOCUMENTS
DE    2825232 C2    12/1978
(Continued)

OTHER PUBLICATIONS

Abstract for JP2002151395.
German Search Report.

*Primary Examiner* — Nicholas Lucchesi
*Assistant Examiner* — Aarti B Berdichevsky
(74) *Attorney, Agent, or Firm* — K&L Gates LLP (57) ABSTRACT

An applicator for applying functional substances, such as cosmetic powder, food color marking, India ink effect marks, or drugs into human skin, having a base, a plurality of microneedles fixed to and projecting from the base a distance only sufficient to penetrate into the stratum corneum or dermis, with the microneedles being of a material that is capable of disintegration and dispersion into the stratum corneum or dermis, such as maltose. The needles contain the functional substance for delivery into the stratum corneum or dermis. The microneedles are of a length approximately 0.5 to 500 μm when used to apply a functional substance to the stratum corneum, or are of a length of approximately 500 to 5,000 μm when used to apply a functional substance to the dermis.

34 Claims, 6 Drawing Sheets

U.S. PATENT DOCUMENTS

| | | | |
|---|---|---|---|
| 2002/0099356 A1 | 7/2002 | Unger et al. | 604/501 |
| 2002/0133129 A1* | 9/2002 | Arias et al. | 604/272 |
| 2002/0138049 A1 | 9/2002 | Allen et al. | |
| 2002/0188245 A1 | 12/2002 | Martin et al. | 604/46 |
| 2003/0097078 A1 | 5/2003 | Maeda | 600/509 |
| 2003/0199812 A1 | 10/2003 | Rosenberg | |
| 2003/0208167 A1 | 11/2003 | Prausnitz et al. | |
| 2004/0010237 A1* | 1/2004 | D'Ussel | 604/272 |
| 2004/0087893 A1 | 5/2004 | Kwon | 604/46 |

FOREIGN PATENT DOCUMENTS

| | | |
|---|---|---|
| DE | 697 20 057 T2 | 12/1997 |
| DE | 100 65 168 A1 | 7/2002 |
| JP | 2003238347 | 8/2003 |
| WO | WO 98/28037 | 7/1998 |
| WO | WO 99/64580 | 12/1999 |
| WO | WO 00/74763 | 12/2000 |
| WO | WO 2004/000389 A2 | 12/2003 |
| WO | WO 2004/033021 A1 | 4/2004 |

* cited by examiner

APPLICATOR FOR APPLYING FUNCTIONAL SUBSTANCES INTO HUMAN SKIN

FIELD OF THE PRESENT INVENTION

The present invention relates to the use of microneedle applicators for applying functional substances into human skin and the method of producing microneedles for this purpose.

BACKGROUND OF THE PRESENT INVENTION

Presently, modifying the appearance of or treating the human skin with liquid substances or powders has normally been accomplished by topographical application to the surface of the skin. For example, prior applications have been used to attempt to eliminate cornified portions of the skin in both chemical and nutritional ways, but cornification is a complicated biological phenomenon as well as being a problem, primarily occurring in the aging process. With the known types of application the substance is only temporarily retained as such substances are readily removed by perspiration, washing, unintentional contact with foreign materials and various weather conditions, making it necessary to reapply the substances on a daily or more frequent, basis. Further, any desired depth of penetration into the skin has been difficult to accurately control. Thus, there are major problems in the convenience, effectiveness, and effort in conventional applications.

Also, needles are commonly used to inject drugs, such as insulin, interferon, and pain killers, into the skin or flesh of patients, but these conventionally penetrate considerably deeper than necessary and cannot be controlled reliably as to the depth of penetration. Furthermore, they often cause pain to the patient.

Thus, there are major problems in convenience, effectiveness and effort in applying functional substances using these known types of application.

BRIEF SUMMARY OF THE PRESENT INVENTION

The purpose of the present invention is to apply functional substances into the human skin, particularly into the stratum corneum to enhance the appearance of the skin, to provide cosmetic effects or chemically improve the skin or into the dermis to apply drugs to the body. By the present invention, it is possible to conveniently, safely and effectively modify or provide a desired functional effect to the surface of the skin or to apply drugs into the body using microneedles that penetrate to a controlled depth, and, do not create any undesirable sensation or pain in application. In addition, the present invention provides an effective method of producing microneedles for use in the aforesaid application.

Basically, the applicator of the present invention includes a base with a plurality of microneedles fixed to the base and projecting therefrom a distance sufficient to penetrate into the skin. The microneedles are made of a material that is capable of disintegration and dispersion into the skin when the microneedles are inserted into the skin. A functional substance is carried by the microneedles for delivery by the microneedles into the skin. The functional substance may be distributed in the material of the microneedles, such as being homogeneously distributed throughout the microneedle material, or the functional substance may be retained in recesses in the microneedles or retained in capsules that are retained in the microneedles. Preferably, the microneedles project from the base approximately 0.5 to 500 µm in applying functional substances to the stratum corneum or project approximately 500 to 5,000 µm in applying functional substances to the dermis. The microneedles may be cone-shaped, rectangular, square or at least partially elliptical in cross-section or any other desired shape. Preferably, the shortest side or cross-sectional dimension at the base of the microneedles is approximately 0.1 to 100 µm.

Also, preferably, the microneedles are formed to facilitate breaking off at least the outer portions in the skin when the base is removed. This can be facilitated by the microneedles having restrictions intermediate their ends or having a step between thick inner portions and thin outer portions or having barbed tips.

To facilitate insertion of the microneedles, the tips may be knife-shaped.

In one form of the invention, microcontainers containing functional substances are contained within the microneedles, preferably in recesses or within barbed tips of the microneedles. In another form, the microneedles are formed with capillary recesses in the outer portions thereof for retaining the functional substances for delivery into the skin.

The method of producing microneedles according to the present invention includes forming a microneedle pattern by x-ray lithography that irradiates an x-ray sensitive photopolymer using synchrotron x-ray radiation, then forming a mold in the reverse form of the microneedle pattern by electrotype processing. Then injection molding or casting the microneedles in the mold.

In the preferred embodiment, the material of the microneedles is a sugar that readily disintegrates upon insertion of the microneedles into the skin. Other suitable materials may be used that disintegrate into the skin upon insertion of the microneedles into the skin.

In the preferred embodiment, the x-ray sensitive photopolymer is a polymer containing polymethyl methacrylate.

In one form of the method, a functional substance is distributed, preferably homogeneously, in the material of the microneedles prior to molding.

Various modifications and improvements of the invention as disclosed herein are contemplated as being within the scope of the present invention, which is not to be limited by the specific disclosure or the accompanying drawings. The invention is intended to be limited only to the scope of the appended claims.

BRIEF DESCRIPTION OF THE DRAWINGS

Further features, embodiments, and advantages of the present invention will become apparent from the following detailed description with reference to the drawings, wherein:

FIGS. 14 a, b, c and d are illustrations of alternative knife-shaped outer ends of microneedles of the present invention.

DETAILED DESCRIPTION OF PREFERRED EMBODIMENTS

The present inventors are the inventors of the subject matter of Japanese Patent No. 2003238347, dated Aug. 27, 2003, which subject matter, as well as additional subject matter, is included in the present application.

Figure 1:
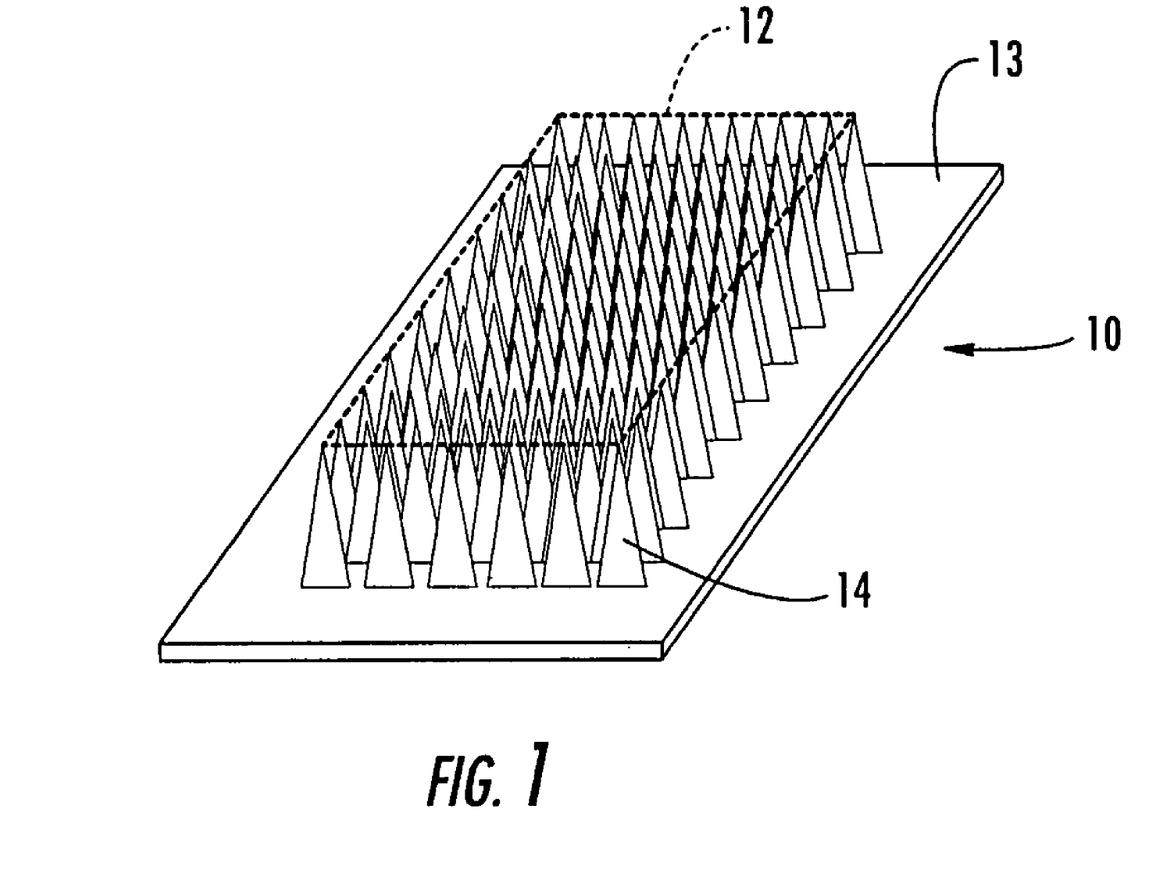
FIG. 1 is a greatly enlarged perspective view of an applicator incorporating the preferred embodiment of the present invention.
Figure 2:
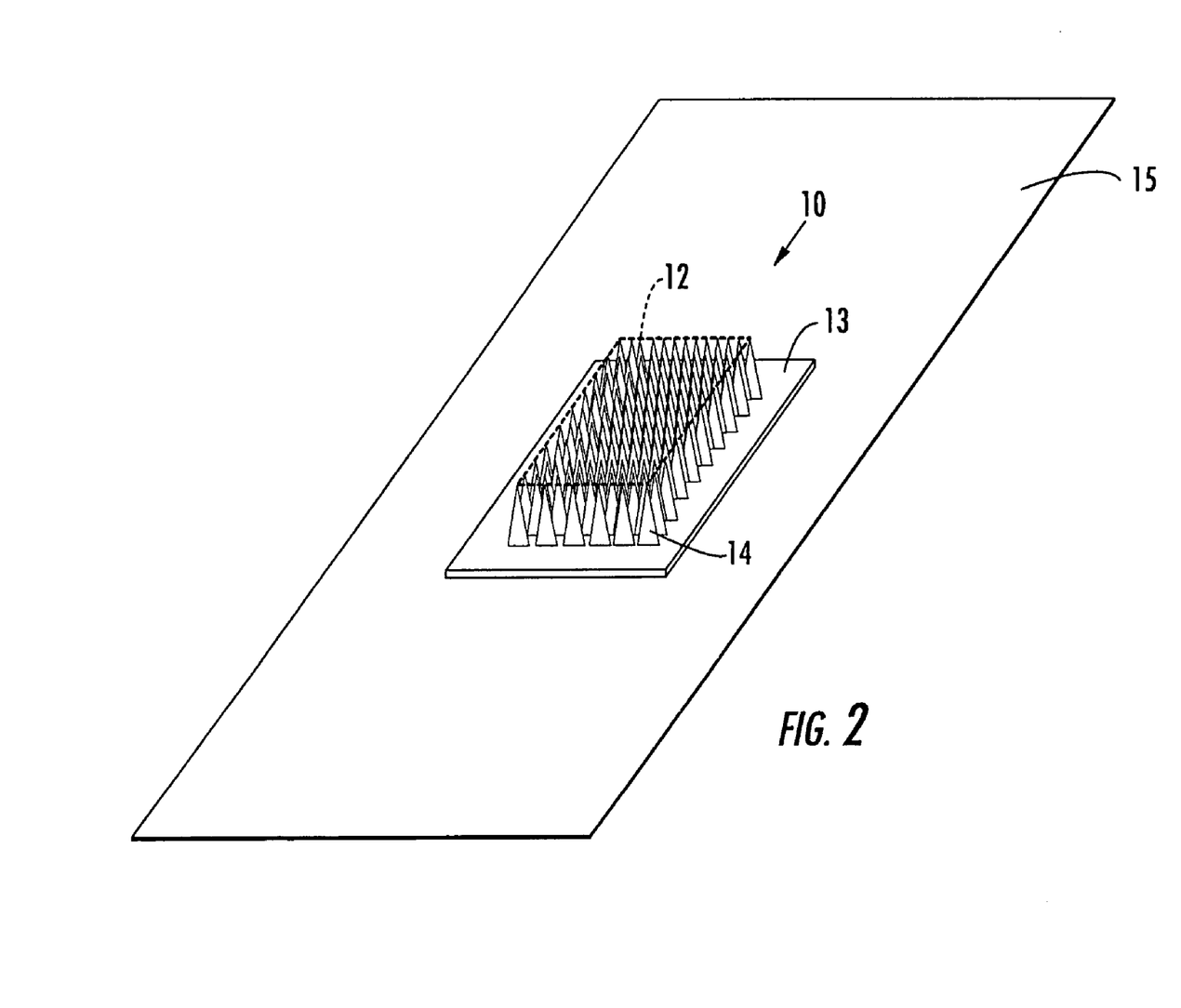
FIG. 2 is a perspective view of the applicator of FIG. 1 attached to a tape used for adhering the applicator to the skin of a human.

A preferred embodiment of the applicator of the present invention is illustrated in FIG. 1. As illustrated, it is made up of a mass 12 of a plurality of microneedles attached to and projecting from a base 13. The mass 12 contains thousands of individual microneedles that are not discernible to the naked eye. For illustrative purposes, the applicator 10 is illustrated in FIG. 1 in greatly enlarged proportion and with microneedles 14 in the mass 12 being illustrated in greatly reduced number for clarity of illustration.

As used herein, a microneedle is a needle having a length dimension in the micron range.

In the preferred embodiment, the microneedles 14 are fixed to the base 13 and project therefrom a distance sufficient to penetrate into the skin when the applicator 10 is pressed against the skin of a human. This projecting distance, when applying a functional substance into the stratum corneum, is preferably in the range of approximately 0.5 to 500 µm. When the applicator is used to apply functional substances into the dermis, the projecting distance or height of the microneedles is preferably in the range of approximately 500 to 5,000 µm.

The microneedles 14 are made from a suitable material that is capable of disintegration and dispersion into the stratum corneum or dermis upon insertion of the microneedles 14 into the skin. A preferred material is sugar, such as a material that is primarily 97% maltose and 3% dextran. For ease of manufacture, the microneedles 14 and the base 13 are formed integrally of the same material. Other materials may be mixed with the primary material to provide modified characteristics, such as slower release. For example, poly lactic acid may be added to slow the rate of dispersion. Materials other than sugar may be used in place of sugar that are capable of disintegrating and dispersing into the stratum corneum or dermis. For example, poly lactic acid could be used instead of sugar.

The purpose of the applicator is to apply functional substances to the stratum corneum or the dermis. For cosmetic purposes, the functional substance is preferably applied to the stratum corneum and may be a cosmetic powder, such as barium sulfate colored to a desired skin coloring, or a red food coloring substance to use as a marking, or India ink for creating a cosmetic affect, or an organic ultraviolet shield material to protect the underlying portion of the skin against ultraviolet sun rays. As the functional substance is applied into the stratum corneum, it will not readily dissipate and can provide a cosmetic effect lasting for a prolonged period of time, from a few days up to several months.

For drug applications, the drugs, such as insulin, interferon, pain killers, or any other appropriate drug, may be applied into the dermis. In the dermis, there is more moisture and it is warmer than the stratum corneum. Therefore, a drug will advantageously dissipate more quickly in the dermis than in the stratum corneum.

The functional substance 15 is carried by the microneedles 14. This may be accomplished by mixing the functional substance 15 with the main material for producing the microneedles 14 prior to forming the material into the microneedles 14. This will produce a homogeneous mix of the functional substance in the material of the microneedles 14.

Figure 4:
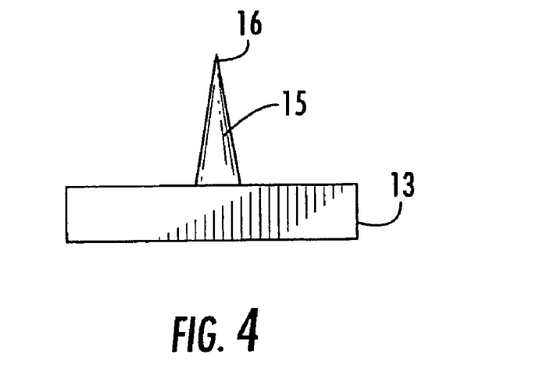
FIG. 4 is an elevational view of one form of the microneedle attached to a base according to the present invention.

With the functional substance 15 distributed in the material of the microneedles 14, the functional substance 15 will be released into the stratum corneum or dermis upon disintegration of the material of the microneedles 14 when the applicator 10 is applied to the skin of a human. A typical microneedle 15 is illustrated in FIG. 4. This microneedle 15 is cone-shaped, tapering from the base 13 to an outer tip 16. In this form, the functional substance is distributed within the material of the microneedle 15.

Figure 5:
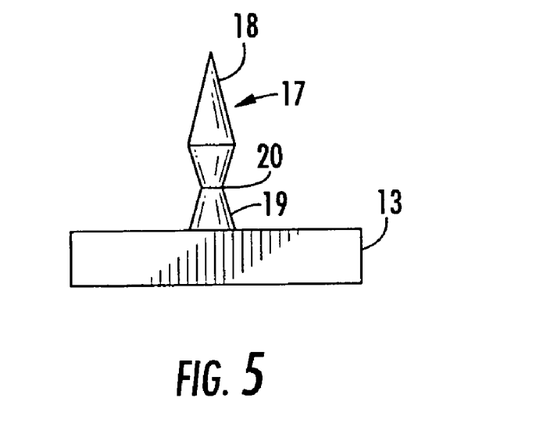
FIG. 5 is a side elevation similar to FIG. 4, showing the microneedle formed with a constriction between its ends.

To facilitate severing or breaking off the outer portion of a microneedle in the skin, the microneedle 17 of FIG. 5 is formed with a conical outer portion and a constriction 20 between the ends of the microneedle to facilitate breaking off the outer portion 18 at the constriction 20 upon manipulation of the base 13.

Figure 6:
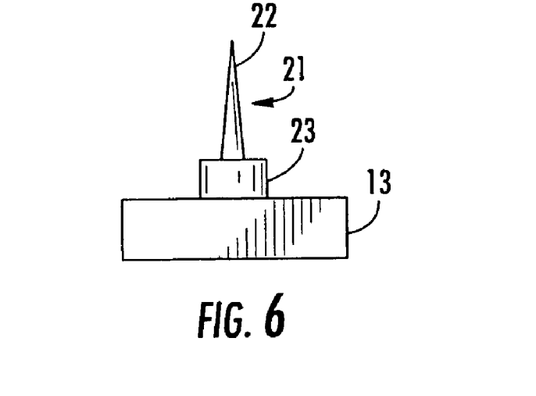
FIG. 6 is a side elevation similar to FIG. 4, showing the microneedle having a thin outer portion and a thick inner portion.
Figure 7:
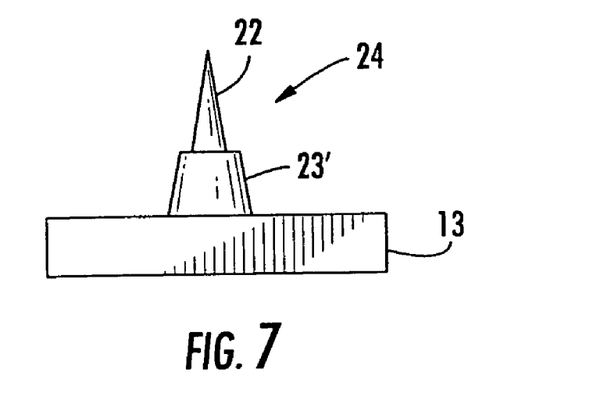
FIG. 7 is a side elevation similar to FIG. 6, showing the microneedle having the thicker inner portion tapered.

An alternative form of a microneedle that is formed to facilitate severing or breaking off the outer portion is illustrated in FIG. 6. In this embodiment the microneedle 21 is formed with a conical outer portion 22 and an enlarged cylindrical inner portion 23, with the intention that the outer portion 22 will break off from the inner portion 23 upon manipulation of the base 13. FIG. 7 illustrates a similar needle 24 in which the inner portion 23' is tapered.

Figure 8:
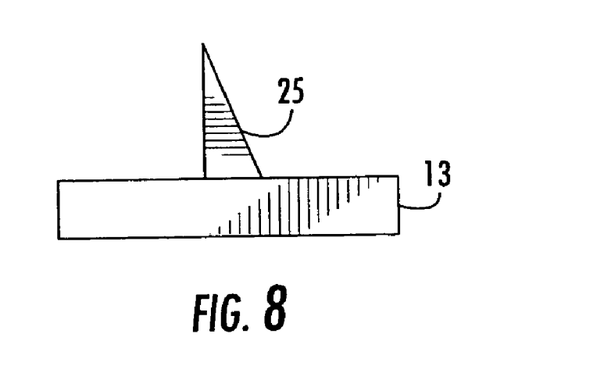
FIG. 8 is a side elevation similar to FIG. 4, showing the microneedle in a prism shape.
Figure 9:
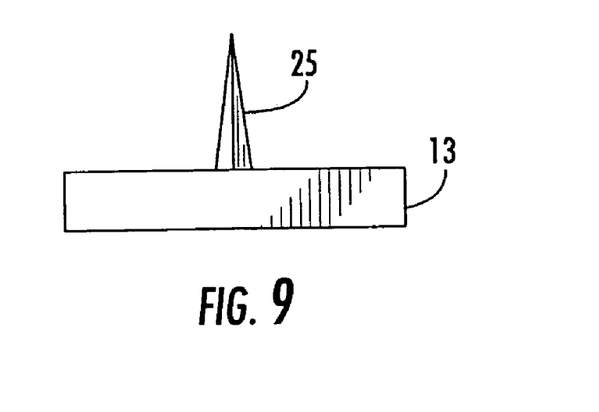
FIG. 9 is a side elevation of the microneedle and base of FIG. 8 looking from the right in FIG. 8.

Another alternative shape of the microneedle is illustrated in FIGS. 8 and 9. In this embodiment the microneedle 25 is formed as a three-sided tapered prism.

Rather than having the functional substance distributed in the material of the microneedle 14, the functional substance may be carried by the microneedle 14 from the material of the microneedle, such as in a recess, with the functional substance being retained in the recess by capillary attraction or by being encapsulated in a dissolvable or otherwise disintegratable microcontainer. Concentrating the functional substance in a recess rather than distributing the functional substance in the material of the microneedle and base, requires more complicated manufacture, but may be necessary where the functional material is not compatible with mixing in the main material of the microneedle, and may be preferable where the functional substance is expensive and significant amounts would be wasted in the base that is not inserted into the skin.

Figure 10:
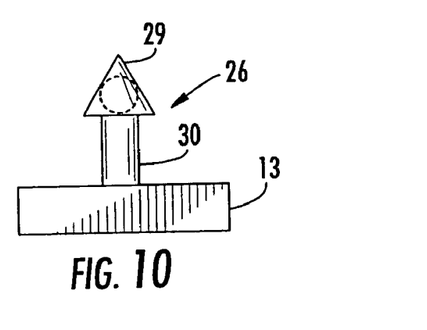
FIG. 10 is a side elevation similar to FIG. 4, illustrating the microneedle with a barbed tip at its outer end.
Figure 11:
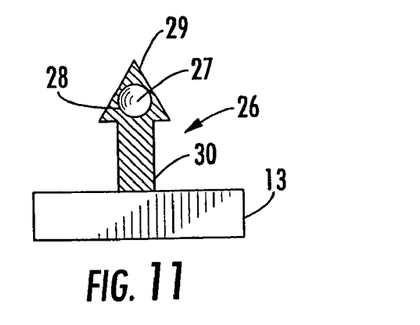
FIG. 11 is a vertical sectional view of the microneedle and base of FIG. 10.

A microneedle 26 carrying the functional substance separately is illustrated in FIGS. 10 and 11. In this embodiment, the functional substance 27 is encapsulated in a spherical microcontainer 28, which is embedded in the barbed tip 29 of the microneedle 26. This barbed tip 29 configuration also facilitates separation of the tip 29 when the base 13 is removed from the skin. The microcontainer 28 may preferably be made from the same sugars or other material as the material of the microneedle 26. It can be used with substances such as insulin or vitamin C or substances that are not compatible with the microneedle material or are too expensive for use if they were mixed throughout the microneedle material.

Figure 12:
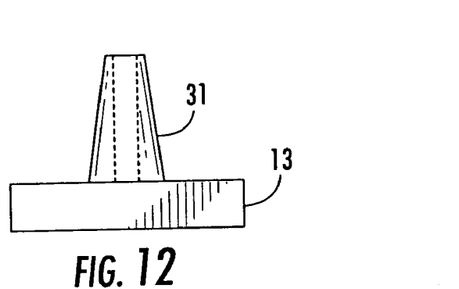
FIG. 12 is a side elevation similar to FIG. 4, illustrating the microneedle with a central recess extending therethrough.
Figure 13:
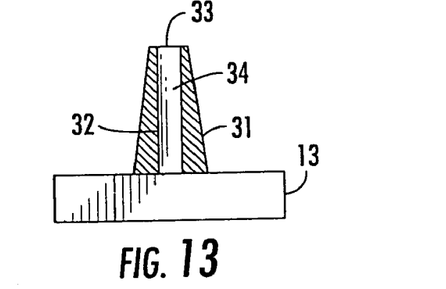
FIG. 13 is a vertical sectional view of the microneedle and base of FIG. 12.
Figure 14A:
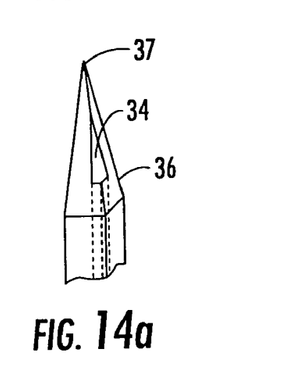
Figure 14B:
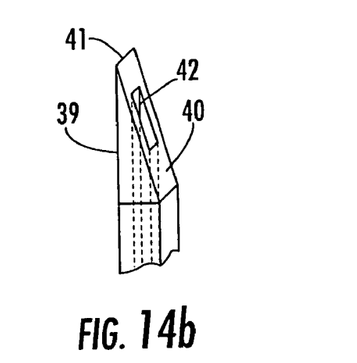
Figure 14C:
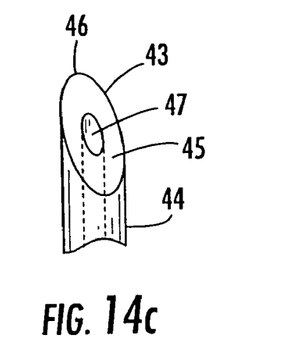
Figure 14D:
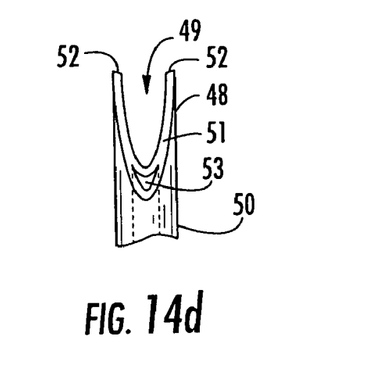

Capillary retention of the functional substance in a microneedle is illustrated in FIGS. 12 and 13. In this embodiment, the microneedle 31 is in the shape of a truckcated cone. A cylindrical recess 32 is formed in the microneedle 31 extending from an open end 33 centrally along the axis of the microneedle through the full length of the microneedle 31. In this embodiment, a functional substance 34 is retained in the recess 32 and is released into the stratum corneum or dermis upon disintegration of the material of the microneedle 31. Typically, such a recess may be 10-100 μm in diameter.

To facilitate painless insertion of the microneedles into the skin, particularly with the longer needles that are intended to penetrate the dermis, the tips of the needles may be formed as knife points as illustrated in FIGS. 14 a, b, c and d. The needle point 36 illustrated in FIG. 14a tapers sharply on all sides to a sharp tip 37 with the recess 38 opening at a spacing from the tip 37 so as not to result in any blunting of the tip. The needle point 39 illustrated in FIG. 14b has one side 40 that tapers sharply to a sharp edge 41 at the top of an opposite side, with the recesses 42 opening along the side 40 short of the sharp edge 41 so as not to interfere with the sharp edge 41. The needle point 43 illustrated in FIG. 14c is formed on the end of a cylindrical or conical microneedle 44 with an inclined surface 45 that inclines sharply to an outer tip 46, with the recess 47 opening along the inclined surface 45. The needle point 48 illustrated in FIG. 14d is bifurcated, formed by a U-shaped cut 49 in the outer end of a cylindrical or conical microneedle 50 with inclined surfaces 51 that incline to sharp tips 52. The recess 53 opens into the base of the U-shaped cut 49.

The applicator 10 is preferably produced by first creating a master pattern by using synchrotron x-ray radiation through a mask with a specific pattern to irradiate an x-ray sensitive photopolymer foundation containing polymethyl methacrylate, which is then developed to eliminate the irradiated portion. This is preferably done with the microfabrication technology disclosed in Japanese Patent No. 2002151395, dated May 24, 2002, the substance of which is incorporated herein by reference. This technology is further developed, making micron-size high precision processing easy by applying ultra-short wave length x-rays produced by the synchrotron x-ray radiation. A mold is then formed from the master pattern using a process such as electrotyping or machine processing, which forms a reverse profile to that of the master pattern. The mold may be made, for example, from nickel, titanium, stainless steel, or any other suitable material or alloy.

For microneedles of the larger size that are used to insert into the dermis, the pattern may be made by ultraviolet lithography in which an ultraviolet photopolymer is irradiated by ultraviolet rays.

After forming the mold, the material of the microneedle 14 and base 13 is formed in the mold by injection molding or casting to produce the final integral microneedle 14 and base 13 product.

Figure 3:
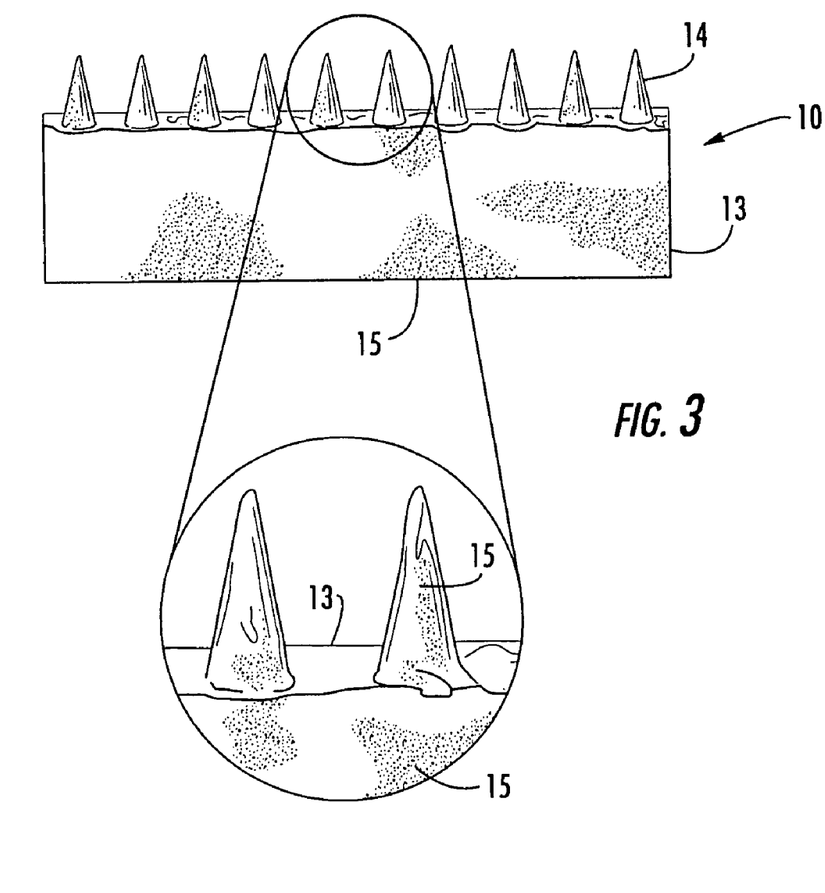
FIG. 3 is a side perspective view of the applicator of FIG. 1.

The applicator 10 or a plurality of applicators may be retained temporarily on the skin by fixing the applicators 10 on an adhesive tape 35, such as medical tape, as illustrated in FIG. 3, and adhering the tape 11 onto the skin.

The following examples disclose ways in which the present invention may be practically utilized, but it is understood that these examples are not limiting as the present invention has application in many other ways that would be appreciated by one skilled in the art.

EXAMPLE 1

The applicator is used to mask or eliminate a discolored or undesirably colored portion of the skin of a face. The microneedle and base material is produced with a functional cosmetic powder of a similar color to the test subject's skin distributed homogeneously in the material of the microneedle. Multiple applicators can be utilized where the area to be treated is relatively large. As the normal thickness of a skin's stratum corneum is normally over 100 μm and under 300 μm, a microneedle height of 50 μm to 70 μm is used with the width of the tip being under 5 μm to avoid inflicting any pain.

Ten thousand 60 μm long, 10 μm diameter conical needles formed of maltose, mixed with 20% by weight of a functional cosmetic powder, were created according to the production method described hereinabove and were formed on a 1 cm square base 35.

The applicator was lightly applied to the test subject's facial area, tapped by hand about 10 times, and the base removed, leaving the microneedles, or at least outer portions of the microneedles, in the skin. This treatment eliminated any visual difference in appearance from the surrounding skin area.

A variation of this example uses a conical microneedle 150 μm in length of a diameter at the base of 50 μm and a diameter at the tip of 5 μm. It uses a material comprising 95% maltose, 3% dextran and 2% vitamin C.

EXAMPLE 2

There is a potential problem in misidentifying new born babies with the tragic result of babies being associated with the wrong mother. In an attempt to avoid such mishaps, ribbons, pen markings and labels are used, but these are frequently lost during handling or movement of the newborns. In this example, markings can be implanted in the stratum corneum of a newborn's skin to provide a safely retained identification unaffected by handling or activity of the newborn.

In this example, 2,500 70 μm long, 20 μm diameter conical microneedles formed of maltose material mixed with 15% by weight of red food coloring were created according to the production method described above, on a 0.5 cm square base. The applicator was lightly applied to the test subject's skin (for test purposes, an adult subject was used, rather than a new born) and tapped by hand about 10 times. The base was then removed. A 0.5 cm square red color marking resulted. The red coloring remained until it completely disappeared after approximately two months.

EXAMPLE 3

In the field of entertainment, actors and other performers often desire skin markings that replicate beauty marks or otherwise provide a desirable effect. There is, therefore, a high demand for reproducibility in makeup techniques, which can be obtained easily and quickly by the present invention. New methods of expression can thus be provided, supporting the creation of a new entertainment culture, which technique can also be utilized for effect by the public at large.

For this purpose, an applicator may be produced having 60 μm long 15 μm diameter circular needles formed from maltose mixed with 10% by weight of India ink, formed on a 0.3 cm diameter circular base. This would be lightly applied to the back of a hand of a test subject, tapped by hand about 10 times and then removed, leaving portions of the microneedles in the skin. As a result, a 0.3 cm diameter circular beauty mark would be easily created without pain to the test subject. It is expected that a beauty mark would result that would remain for approximately 3 months.

EXAMPLE 4

Cosmetic powders or oils are conventionally used on the face or other parts of the body as a sun block, but these often lose there effectiveness as they are easily removed through sweating, bathing, washing or other contact with foreign objects. By the present example, sun block material can be implanted shallowly in the face or body skin otherwise to provide a sun block that can be sustained for a few days, making it far more effective than conventionally applied sun block products.

For this purpose, 70 μm long, 10 μm diameter conical microneedles are formed of maltose mixed with 1% by weight of parasol MCX (octylmethoxycinnamate), an organic ultraviolet shield. The microneedles are formed on a 1 cm diameter circular base. This was lightly applied to the back of the hand of the test subject, tapped by hand about 10 times, and then removed, leaving portions of the microneedles in the stratum corneum. For the following month, the test subject exposed the back of the hand to direct outdoor sunlight and the extent of sunburn was examined. The result was that a 1 cm diameter circular portion of the skin was not as sunburned as the surrounding parts and there was no sunburn sensation experienced by the test subject in that area. The sun block effect disappeared after approximately 2½ months.

As established by the foregoing examples, the applicator of the present invention can be used to apply functional cosmetic powders, such as artificial colorings, such as ultraviolet absorbers, and the functional substance can be inserted into the skin's stratum corneum by leaving the tip or part of the microneedle within the skin. The main material of the microneedles being sugar, the portions of the microneedles that remain in the skin disintegrate and disperse into the skin and ultimately into the body, being harmless to the body. The functional substance will be maintained in the skin from a few days to a few months. Thus, the use of the applicator of the present invention is painless, safe, effective and easily applied.

EXAMPLE 5

It is contemplated that aspirin (acetylsalicylic acid) can be mixed in sugar material in a ratio of 95% maltose, 3% dextran and 2% aspirin and formed into needles, such as illustrated in FIG. 4, 1,000 μm long, 500 μmin diameter at the base and 5 μm in diameter at the tip.

By the present invention, functional substances can be implanted into the skin in a painless manner with the substance being applied in a stable condition during the skin's renewal process, allowing the functional substance to remain in the stratum corneum for extended periods of time, obviating the necessity to repeatedly apply functional substances topographically to the skin on a daily basis. Further, by using sugars as the material for the microneedles, the material is dissipated within the skin and even within blood vessels if the insertion is accidentally to a greater depth than intended, making the application safe. Further, when applied to the depth of the dermis, a substance that is capable of disintegrating into the body can do so readily. If the substance is not disintegratable, such as tattoo material, it will remain substantially permanently if applied into the demis.

In view of the aforesaid written description of the present invention, it will be readily understood by those persons skilled in the art that the present invention is susceptible of broad utility and application. Many embodiments and adaptations of the present invention other than those herein described, as well as many variations, modifications, and equivalent arrangements, will be apparent from or reasonably suggested by the present invention and the foregoing description thereof, without departing from the substance or scope of the present invention. Accordingly, while the present invention has been described herein in detail in relation to preferred embodiments, it is to be understood that this disclosure is only illustrative and exemplary of the present invention and is made merely for purposes of providing a full and enabling disclosure of the invention. The foregoing disclosure is not intended nor is to be construed to limit the present invention or otherwise to exclude any such other embodiments, adaptations, variations, modifications and equivalent arrangements, the present invention being limited only by the claims appended hereto and the equivalents thereof.

What is claimed is:

1. An applicator for applying functional substances into human skin, comprising:
   (a) a base,
   (b) a plurality of microneedles fixed to said base and projecting therefrom a distance sufficient to penetrate into the skin, said microneedles being made of a material that is substantially sugars that dissolve within the human body and capable of disintegration and dispersion into the skin, and
   (c) a functional substance carried by said microneedles for delivery by said microneedles into the skin.

2. An applicator according to claim 1 and characterized further in that said functional substance is distributed in the material of said microneedles.

3. An applicator according to claim 2 and characterized further in that said functional substance is distributed homogeneously throughout said microneedles.

4. An applicator according to claim 1 and characterized further in that said functional substance is encapsulated in said microneedles.

5. An applicator according to claim 1 and characterized further in that said base and said microneedles are integrally molded from the same material.

6. An applicator according to claim 5 and characterized further in that said functional substance is distributed homogeneously throughout said base and microneedles.

7. An applicator according to claim 1 and characterized further in that said microneedles are generally cone shaped.

8. An applicator according to claim 1 and characterized further in that said microneedles are square in cross-section.

9. An applicator according to claim 1 and characterized further in that said microneedles are polygonal in cross-section.

10. An applicator according to claim 1 and characterized further in that said microneedles are at least partially elliptical in cross-section.

11. An applicator according to claim 1 and characterized further in that said microneedles are constricted intermediate their ends to facilitate breaking off the portions of the needles beyond the narrow portions to leave those portions in the skin.

12. An applicator according to claim 1 and characterized further in that said microneedles have relatively thin outer portions and relatively thick inner portions adjacent said base with a step between said portions to facilitate separation of said outer portions from said inner portions with the outer portions remaining in the skin.

13. An applicator according to claim 1 and characterized further in that said microneedles have tips that are knife-shaped to facilitate insertion into the skin.

14. An applicator according to claim 1 and characterized further by microcontainers containing said functional substance, said microcontainers being contained within said microneedles for delivery into the skin.

15. An applicator according to claim 14 and characterized further in that said microneedles are formed with barbed tips and said microcontainers are disposed in said barbed tips for separation with the barbed tips from the remainder of the microneedles for retention in the skin upon removal of the base.

16. An applicator according to claim 1 and characterized further in that said microneedles have capillary recesses in outer portions thereof for retaining said functional substances for delivery into the skin.

17. An applicator according to claim 16 and characterized further in that said capillary recesses extend along a central axis of said microneedles and are open at the outer ends of said microneedles.

18. An applicator according to claim 1 and characterized further in that said microneedles project from said base a distance sufficient to penetrate the stratum corneum.

19. An applicator according to claim 18 and characterized further in that said microneedles project approximately 0.5 to 500μm from said base.

20. An applicator according to claim 19 and characterized further in that said microneedles are generally cone shaped with the diameter at said base being approximately 0.1 to 100μm.

21. An applicator according to claim 19 and characterized further in that said microneedles are square in cross-section with the sides being approximately 0.1 to 100μm at said base.

22. An applicator according to claim 19 and characterized further in that said microneedles are polygonal in cross-section with the sides being approximately 0.1 to 100μm at said base.

23. An applicator according to claim 19 and characterized further in that said microneedles are at least partially elliptical in cross-section with a shortest diameter of 0.1 to 100μm at said base.

24. An applicator according to claim 1 and characterized further in that said microneedles project from said base a distance sufficient to penetrate the dermis.

25. An applicator according to claim 24 and characterized further in that said microneedles project approximately 500 to 5,000μm from said base.

26. An applicator according to claim 25 and characterized further in that said microneedles are generally cone shaped with the diameter at said base being approximately 0.1 to 1,000μm.

27. An applicator according to claim 25 and characterized further in that said microneedles are square in cross-section with the sides being approximately 0.1 to 1,000μm at said base.

28. An applicator according to claim 25 and characterized further in that said microneedles are polygonal in cross-section with the sides being approximately 0.1 to 1,000μm.

29. An applicator according to claim 24 and characterized further in that said microneedles are at least partially elliptical in cross-section with a shortest diameter of 0.1 to 1,000μm at said base.

30. An applicator according to claim 1 and characterized further in that said material is substantially maltose.

31. An applicator according to claim 1 and characterized further in that said microneedles have relatively thick inner portions and relatively thick outer portions with constricted intermediate portions therebetween to facilitate separation of said outer portions from said inner portions with the outer portions remaining in the skin.

32. An applicator for applying functional substances into human skin, comprising:
(a) a base,
(b) a plurality of microneedles fixed to said base and projecting therefrom a distance sufficient to penetrate into the skin, said microneedles being made of a material that is capable of disintegration and dispersion into the skin,
(c) a functional substance carried by said microneedles for delivery by said microneedles into the skin, and
(d) said microneedles having relatively thick inner portions and relatively thick outer portions with constricted intermediate portions therebetween to facilitate separation of said outer portions from said inner portions with the outer portions remaining in the skin.

33. An applicator for applying functional substances into human skin, comprising:
(a) a base,
(b) a plurality of microneedles fixed to said base and projecting therefrom a distance sufficient to penetrate into the skin, said microneedles being made of a material that is capable of disintegration and dispersion into the skin, and
(c) microcontainers containing said functional substance, said microcontainers being contained within said microneedles for delivery into the skin.

34. An applicator according to claim 33 and characterized further in that said microneedles are formed with barbed tips and said microcontainers are disposed in said barbed tips for separation with the barbed tips from the remainder of the microneedles for retention in the skin upon removal of the base.

* * * * *